United States Patent [19]

Tanihara et al.

[11] Patent Number: 5,192,684
[45] Date of Patent: Mar. 9, 1993

[54] HUMAN IGG₁ MONOCLONAL ANTIBODY SPECIFIC FOR THE NICOTINIC ACETYLCHOLINE RECEPTOR AND HYBRIDOMA PRODUCING THE ANTIBODY

[75] Inventors: Masao Tanihara; Hideaki Yamada, both of Kurashiki; Toshihide Nakashima, Toyonaka; Yoshiaki Omura, Mitsu; Koichi Takakura, Nishinomiya, all of Japan

[73] Assignee: Agency of Industrial Science & Technology, Ministry of International Trade & Industry, Tokyo, Japan

[21] Appl. No.: 175,304

[22] Filed: Mar. 30, 1988

[30] Foreign Application Priority Data

Sep. 8, 1987 [JP] Japan .................................. 62-223174

[51] Int. Cl.⁵ .................... C12N 5/24; C12N 15/02; C07K 15/28; C12P 21/08
[52] U.S. Cl. .................... 435/240.27; 530/388.15; 530/388.22; 435/172.2; 435/70.21
[58] Field of Search .............. 530/387, 388.15, 388.22; 435/240.27, 172.2, 70.21; 935/104, 108, 110

[56] References Cited

FOREIGN PATENT DOCUMENTS 231024 12/1984 Japan .

OTHER PUBLICATIONS

Kamo et al., Science 215: 995 1982.
Mittag et al., New England Journal of Medicine 294: 691 1976.
Tzartos et al., PNAS USA 77: 755, 1980.
Buck et al., pp. 275-309 in: Kennett et al. Eds. "Monoclonal Antibodies and Functional Cell Lines" Plenum Press 1984.
Chemical Abstract No. CA105(21): 189033p, Blair et al., Immunol. Invest. 15(4) 351-64 1986.

Primary Examiner—David L. Lacey
Assistant Examiner—Paula Hutzell
Attorney, Agent, or Firm—Oblon, Spivak, McClelland, Maier & Neustadt

[57] ABSTRACT

A human IgG₁ type monoclonal antibody which possesses a molecular weight in the range of 180,000±20,000 as measured by the method of polyacrylamide gel electrophoresis performed in the presence of sodium dodecyl sulfate and is specific to nicotinic acetylcholine receptor. The human IgG₁ type monoclonal antibody mentioned above is produced by a method which comprises fusing human cells capable of producing an antibody against nicotinic acetylcholine receptor with propagable human cells thereby giving rise to a hybridoma capable of producing the aforementioned human IgG₁ type monoclonal antibody, selecting the hybridoma from the production of the fusion, culturing the hybridoma thereby giving rise to the aforementioned human IgG₁ type monoclonal antibody, and selecting the antibody from the cultured medium. The hybridoma mentioned above is also identified.

2 Claims, 4 Drawing Sheets

FIG.3 (1)
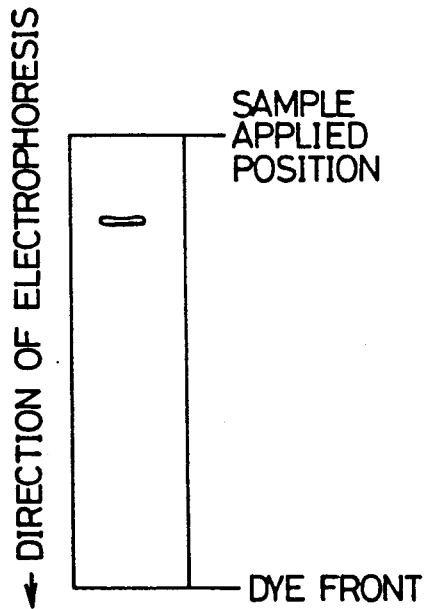
FIG.3 (2)
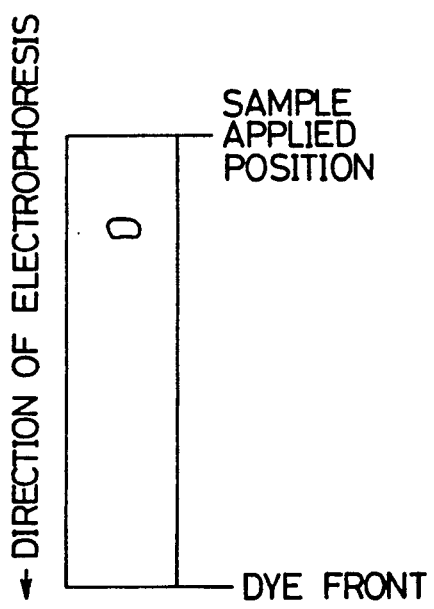

HUMAN IGG$_1$ MONOCLONAL ANTIBODY SPECIFIC FOR THE NICOTINIC ACETYLCHOLINE RECEPTOR AND HYBRIDOMA PRODUCING THE ANTIBODY

BACKGROUND OF THE INVENTION

1. Field of the Invention

This invention relates to a human IgG$_1$ type monoclonal antibody, a method for the production thereof, and a hybridoma capable of producing the antibody.

The human IgG$_1$ type monoclonal antibody provided by the present invention is specific to the nicotinic acetylcholine receptor (hereinafter referred to as "AChR" for short). It is useful in the diagnosis of myasthenia gravis which is characterized mainly by impairment of neuromuscular transmission caused by the presence of autoantibodies against the AChR present on the postsynaptic membrane of the neuromuscular junction and is also useful as a raw material for the production of an antiserum or monoclonal antibody against the aforementioned autoantibodies which is expected to be utilized in the treatment of myasthenia gravis.

2. Prior Art Statement

It has been reported in the literature [Proceedings of the National Academy of Sciences of the United States of America, Vol. 77, pages 755–759 (1980)] that a hybridoma was obtained by fusing the spleen cells of rats immunized with an acetylcholine receptor extracted from the electric organ of torpedos or electric eels with the myeloma cell line originating in mice and a rat monoclonal antibody against acetylcholine receptor was obtained by using the hybridoma mentioned above. Production of a human monoclonal antibody against acetyl choline receptor by the use of a transformed cell line obtained by transforming the lymphocytes collected from the thymus of a patient of myasthenia gravis with Epstein-Barr virus has been reported in literature [Science, Vol. 215, pages 995–997 (1982)]. It has been known to the art that a human monoclonal antibody similar to the autoantibody against acetylcholine receptor possessed by a patient of myasthenia gravis is produced by using a hybridoma which is obtained by fusing peripheral mononuclear cells of a patient of myasthenia gravis with human myeloma cell line resistant to 8-azaguanine [Japanese Patent Public Disclosure SHO 59(1984)-231024].

Generally, when a monoclonal antibody originating in such animals as mice and rats is administered to the human body, the human body induces an immune response to the monoclonal antibody and there may ensue elimination of the activity of the monoclonal antibody and side effects such as systemic shock, because this monoclonal antibody is a protein foreign to the human body. The administration to human bodies of rat monoclonal antibody against acetylcholine receptor, therefore, is not desirable.

In the method for producing the human monoclonal antibody against acetylcholine receptor by using transformed cell lines obtained by transforming lymphocytes collected from the thymus of a patient of myasthenia gravis with Epstein-Barr virus, the antibody-producing ability of the transformed cell lines cannot be rated as very high. Also, detailed information about the human monoclonal antibody obtained by this method is not available.

Regarding the method for producing a human monoclonal antibody against acetylcholine receptor by the use of a hybridoma obtained from peripheral mononuclear cells of a patient of myasthenia gravis and human myeloma cell line, the only information available is the fact that the human myeloma cell line used therein are of the non-secretor secretor type possessing resistance to 8-azaguanine and the fact that the human monoclonal antibody is equivalent to the autoantibody against acetylcholine receptor. It has been known to the art that generally in the production of a hybridoma by the use of human myeloma cell line, the process of production is deficient in fusing efficiency and cloning efficiency and the produced hybridoma is deficient in antibody-producing ability [Journal of Immunological Methods, Vol. 61, pages 17–32 (1983)]. Thus, the aforementioned method in which the hybridoma obtained by the use of human myeloma cell line is utilized can hardly be called advantageous.

OBJECT AND SUMMARY OF THE INVENTION

One object of this invention is to provide a novel human monoclonal antibody which is specific to AChR. Another object of this invention is to provide a method for efficient production of the novel monoclonal antibody. A further object of this invention is to provide a novel hybridoma which is capable of producing the human monoclonal antibody with high efficiency.

The objects described above are accomplished by the present invention providing a human IgG$_1$ type monoclonal antibody which possesses a molecular weight in the range of $180,000 \pm 20,000$ as determined by the method of polyacrylamide gel electrophoresis performed in the presence of sodium dodecyl sulfate and is specific to AChR, a method for the production of a human IgG$_1$ type monoclonal antibody which possesses a molecular weight in the range of $180,000 \pm 20,000$ as determined by the method of polyacrylamide gel electrophoresis performed in the presence of sodium dodecyl sulfate and is specific for AChR, which method is characterized by the steps of fusing human cells capable of producing an antibody against AChR with propagable human lymphoblastoid cell lines, selecting from the product of the fusion a hybridoma capable of producing the human IgG$_1$ type monoclonal antibody mentioned above, culturing the selected hybridoma thereby producing the human IgG$_1$ type monoclonal antibody, and collecting the produced human IgG$_1$ type monoclonal antibody, and a hybridoma obtained by fusing human cells capable of producing an antibody against AChR with propagable human lymphoblastoid cell lines and which hybridoma is capable of producing a human IgG$_1$ type monoclonal antibody which possesses a molecular weight in the range of $180,000 \pm 20,000$ as determined by the method of polyacrylamide gel electrophoresis performed in the presence of sodium dodecyl sulfate and is specific to AChR.

The above and other objects and features of the invention will become more apparent from the following detailed description with reference to the accompanying drawings.

BRIEF DESCRIPTION OF THE DRAWINGS

FIG. 3 (1) shows the electrophoretic pattern of a human IgG$_1$ type monoclonal antibody obtained in Example (6).

FIG. 3 (2) shows the electrophoretic pattern of a commercially available human IgG.

DETAILED DESCRIPTION OF THE PREFERRED EMBODIMENTS

Figure 1:
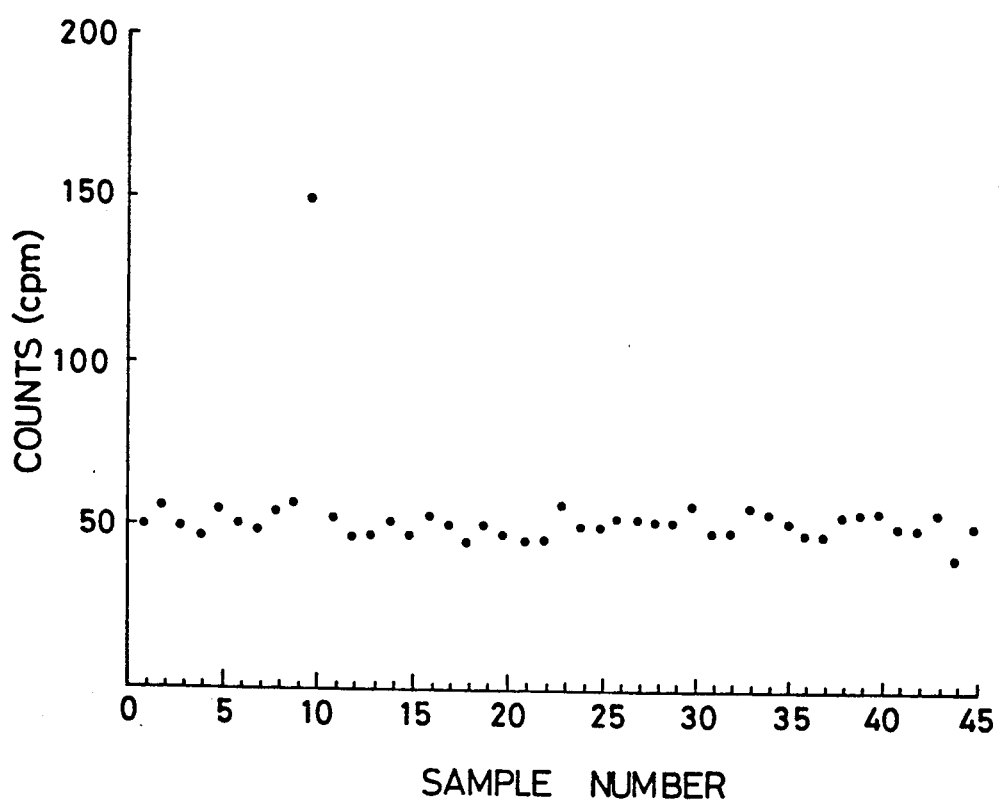
FIG. 1 shows the data on radioactivity obtained in Example (4), for the precipitates (Sample Nos. 1 to 44) formed when the culture supernatants of 44 of the total of 49 hybridomas producing human antibodies were used and the precipitate (Sample No. 45) formed when the culture supernatant of G(Ag$_1$)$_2$-cl 7B strain was used.

The production of the aforementioned hybridoma which is capable of producing a human IgG$_1$ type monoclonal antibody specific to AChR is accomplished by first fusing human cells capable of producing an antibody against AChR (hereinafter referred to as "anti-AChR antibody-producing human cells") with propagable human lymphoblastoid cell line and carrying out a procedure to be described later.

The antibody against AChR is present in the blood of a patient of such diseases of autoimmunity as myasthenia gravis. As concrete examples of the anti-AChR antibody-producing human cells, there can be cited those lymphocytes which are obtained from the thymus, the spleen, the lymph nodes, the peripheral blood, etc. of a patient of the aforementioned diseases of autoimmunity. Since the anti-AChR antibody-producing human cells occur in relatively large amounts at a high concentration in the thymus and the spleen of a patient of myasthenia gravis, it is practical to utilize as the anti-AChR antibody-producing human cells those lymphocytes which are present in the thymus and the spleen of a patient of myasthenia gravis. Propagable human lymphoblastoid cell lines are obtained by infecting human lymphocytes with Epstein-Barr virus, for example, thereby effecting transformation of the human lymphocytes. For the purpose of facilitating the selection of the hybridoma capable of producing the human IgG$_1$ type monoclonal antibody specific to AChR from the used human lymphoblastoid cell lines after cell-fusion, it is proper to use as propagable human lymphoblastoid cell lines 6-thioguanine-resistant cells, 8-azaguanine-resistant cells, or 5-bromodeoxyuridine-resistant cells which possess sensitivity to hypoxanthine-aminopterin-thymidine. As concrete examples of such propagable human lymphoblastoid cell lines, there can be cited G(Ag$_1$)$_2$-cl 7B strain deposited with the Fermentation Research Institute, Agency of Industrial Science & Technology 1-3, Higashi 1-chome, Tsukuba-shi, Ibareki-ken 305, Japan, on Mar. 15, 1988 and assigned the deposit number FERM BP-1797 under the Budapest Treaty; GM4672 strain [Journal of Experimental Medicine, Vol. 158, pages 718-730 (1983)]; H35.1.1,0467.3 strain [Journal of Experimental Medicine, Vol. 156, pages 930-935 (1982)]; KR-4 strain [Proceedings of the National Academy of Sciences of the United States of America, Vol. 79, pages 6651-6655 (1982)]; RH-L4 strain [Journal of Immunological Methods, Vol. 61, pages 17-32 (1983)]; GM1500 6TG-A12 strain [Nature, Vol. 288, pages 488-489 (1980)]; WI-L2-729HF$_2$ strain [Journal of Immunology, Vol. 132, pages 1798-1803 (1984)]; and LICR-LON-HMy-2 strain ]Proceedings of the National Academy of Sciences of the United States of America, Vol. 80, pages 2026-2030 (1983)]. It is particularly desirable to use, among other strains cited above, the G(Ag$_1$)$_2$-cl 7B strain which is excellent in the efficiency of fusion with the anti-AChR antibody-producing human cells, in the efficiency of cloning of the produced hybridoma, and in propagability. The G(Ag$_1$)$_2$-cl 7B strain is obtained by transforming peripheral blood lymphocytes of a patient of rheumatoid arthritis with Epstein-Barr virus and imparting 8-azaguanine resistance to the transformed cell. The G(Ag$_1$)$_2$-cl 7B strain also possesses resistance to ouabain.

The fusion of the anti-AChR antibody-producing human cells with the propagable human lymphoblastoid cell lines is generally carried out in a buffered solution in the presence of a fusing agent, in accordance with any of the conventional methods widely employed for fusion of cells. The anti-AChR antibody-producing human cells and the propagable human lymphoblastoid cell lines are used in proportions such that the ratio of the respective numbers of cells falls generally in the range of about 10:1 to about 1:1, preferably in the range of about 4:1 to about 1.5 to 1. As a fusing agent, polyethylene glycol or Sendai virus (Hemagglutinating Virus of Japan) can be used. In terms of ease of handling and efficiency of fusion, it is desirable to use polyethylene glycol possessing an average molecular weight approximately in the range of 1,000 to 5,000. Properly, this polyethylene glycol is used in an amount such that the concentration thereof in the buffer will fall approximately in the range of 40 to 60% by weight. The fusion of cells is generally carried out by adding anti-AChR antibody-producing human cells and propagable human lymphoblstoid cell lines to an animal cell culture medium or a balanced salts solution, further adding a fusing agent thereto, and stirring the resultant mixture at a temperature of about 37° C. for about 2 minutes. As examples of the animal cell culture medium, there can be cited RPMI-1640 medium, Hanks' MEM (Hanks' minimum essential medium), Eagle's MEM (Eagle's minimum essential medium), and as examples of balanced salts solutions there can be cited Hank's balanced salts solution and Earle's balanced salts solution. Otherwise, the fusion of anti-AChR antibody-producing human cells with propagable human lymphoblastoid cell lines may be carried out by the method of electric fusion.

From the cell mixture produced in consequence of the fusion described, the hybridoma capable of producing a human IgG$_1$ type monoclonal antibody specific to AChR is separated as follows. First, the hybridoma of the anti-AChR antibody-producing human cells and the propagable human lymphoblastoid cell lines is selected from the cell mixture. When cells exhibiting sensitivity to hypoxanthine-aminopterin-thymidine are employed as the human lymphoblastoid cell lines, the hybridoma of the anti-AChR antibody-producing human cells and the human lymphoblastoid cell lines can be selectively propagated by culturing the cell mixture obtained by the fusion in a culture medium containing hypoxanthine, aminopterin, and thymidine (hereinafter this culture medium will be referred to as "HAT culture medium"). The culture in the HAT culture medium yields highly desirable results when the concentration of the cell mixture in the culture medium is adjusted to a value generally in the range of $1 \times 10^6$ to $1 \times 10^7$ cells/ml. The HAT culture medium is prepared, for example, by adding to such an animal cell culture medium as RPMI-1640 medium such an amount of fetal bovine serum as to register a concentration approximately in the range of 10 to 15% by volume and further adding thereto hypoxanthine, aminopterin, and thymidine. The concentrations of hypoxanthine, aminopterin, and thymidine in the HAT culture medium are not particularly limited, the only requirement being that the compounds contained should have an adverse effect on the growth of the hybridoma aimed at. Generally, it is desirable to adjust their concentrations to approximately $1 \times 10^{-4}$ mol/liter, $4 \times 10^{-6}$ mol/liter, and $1.6 \times 10^{-5}$ mol/liter respectively. The culture in the HAT culture medium is carried out in a stationary state in air containing about 5 to 8% of carbon dioxide at a temperature of about 37° C. for a period of about one to four weeks. Then, from the hybridoma which has been selected from the cell mixture, the hybridoma capable of producing an IgG type antibody specific to AChR is selected. The question as to whether a given hybridoma capable of producing an IgG type antibody specific to AChR can be determined, for example, by the mthod of radioimmunoassay (hereinafter referred to as "RIA method") or the method of enzyme-immuno assay (hereinafter referred to as "ELISA method"). When the hybridoma which has been selected as described above is subjected to cloning by the limiting dilution method, for example, there can be obtained a propagable hybridoma strain which is capable of producing an $IgG_1$ type monoclonal antibody specific to AChR. T/G-59(5C) strain deposited with the Fermentation Research Institute, Agency of Industrial Science & Technology on Mar. 15, 1988 and assigned the deposit number FERM BP-1798 under the Budapest Treaty can be cited as an example of such a hybridoma strain. The T/G-59(5C) strain is separated from the hybridoma which is obtained by the fusion of lymphocytes present in the thymus of a patient of myasthenia gravis with the $G(Ag_1)_2$-cl 7B strain.

When the hybridoma obtained as described above is cultured in a culture medium prepared by adding to such an animal cell culture medium as RPMI-1640 medium such an amount of fetal bovine serum as to register a concentration of about 10 to 15% by volume or such a human lymphocyte type cell-quality serum-free culture medium as Hybrity-1 (produced by Nippon Yakuhin Kaihatsu K. K.), in air containing about 5 to 8% of carbon dioxide at a temperature of about 37° C., the culture produces a human $IgG_1$ type monoclonal antibody specific to AChR in consequence of the propagation of the hybridoma strain.

The separation of the human $IgG_1$ type monoclonal antibody specific to AChR from the hybridoma cultured medium can be carried out as follows. To be specific, by centrifuging the hybridoma cultured medium and then subjecting the resultant supernatant to such a treatment of purification as ultrafiltration, gel permeation chromatography, affinity chromatography, or ion-exchange chromatography, the human $IgG_1$ type monoclonal antibody aimed at can be obtained.

The human $IgG_1$ type monoclonal antibody specific for AChR obtained as described above possesses a molecular weight in the range of $180,000 \pm 20,000$. This molecular weight can be determined, for example, by the method of polyacrylamide gel electrophoresis to be performed in the presence of sodium dodecyl sulfate as described in Nature, Vol. 227, pages 680–685 (1970), for example. The electrophoresis for this purpose is carried out, to prevent the human $IgG_1$ type monoclonal antibody from being decomposed in the manner of reduction, in the absence of such a reducing agent as 2-mercaptoethanol.

Now, the present invention will be described more specifically below with reference to a working example. It should be noted, however, that this invention is not limited by the example.

EXAMPLE

(1) Preparation of Thymocytes

The thymocytes were obtained by excising the thymus from a patient of myasthenia gravis, washing the thymus with a Dulbecco's modified Eagle's medium, then pulverizing the washed thymus on a stainless steel mesh, collecting the cells which had passed the mesh, and centrifugally washing the cells three times with a RPMI-1640 medium.

(2) Fusion of Cells

The thymocyte obtained in step (1) above in an amount of $1.04 \times 10^8$ cells and a $G(Ag_1)_2$-cl 7B strain in an amount of $5.2 \times 10^7$ cells were mixed with 1 ml of a mixed solution obtained by the combination of 1 g of polyethylene glycol possessing an average molecular weight of 1,500 and 1 ml of a RPMI-1640 medium and then stirred at a temperature of 37° C. for two minutes. By adding gradually 9 ml of a RPMI-1640 medium to the resultant mixture in a stirred state and then centrifuging the resultant mixture, a cell mixture was obtained in the form of a precipitate. A HAT culture medium was prepared by adding hypoxanthine, aminopterin, and thymidine and fetal bovine serum to a RPMI-1640 medium in amounts such as to register respective concentrations of $1 \times 10^{-4}$ mol/liter, $4 \times 10^{-7}$ mol/liter, $1.6 \times 10^{-5}$ mol/liter, and about 13% by volume. To the HAT culture medium, the aforementioned cell mixture was added in an amount such as to register a concentration of $2.5 \times 10^6$ cells/ml. The culture medium containing cells obtained as described above was dispensed in a unit volume of 0.1 ml into 575 wells of a microwell plate made of polystyrene (6 covered microwell plates each containing 96 wells; produced by Nunc Corp., Denmark) and cultured in a stationary state in the air containing 7% of carbon dioxide at a temperature of 37° C. After 10 to 20 days' culture, growth of hybridoma was recognized in 118 wells.

(3) Screening of Hybridoma Producing Human Antibody

In a phosphate buffered solution (hereinafter referred to as "PBS"), an IgG fraction of goat antiserum against a human IgG (heavy and light chains) (produced by Miles-Yeda Corp., Israel) was dissolved in a concentration of 0.05 mg/ml. The resultant solution was dispensed in a unit volume of 50 μl into the wells of a microwell plate made of polyvinyl chloride (96-well plate; produced by Becton-Dickinson and Company, the U.S.A. and marketed under the tradename "Falcon 3912") and were left standing overnight at 4° C. to effect adsorption of antibody on the plate. The solution was removed from the individual wells. Then a PBS solution containing 5% by volume of fetal bovine serum was dispensed in a unit volume of 300 μl into the wells and then left standing at a temperature of 37° C. for two hours so as to effect blocking of the solid-phase surface which had not adsorbed antibody. The wells were washed with a PBS solution containing 5% by volume of fetal bovine serum. Then, the supernatant of the wells in which growth of hybridoma was recognized in the step (2) above was dispensed in a unit volume of 50 μl to the wells, left standing at 37° C. for one hour, and washed with a PBS solution containing 5% by volume of fetal bovine serum. Anti-human Ig antibody labeled with horseradish-peroxidase (Species-specific Whole Antibody, produced by Amersham & Company, England) was dissolved in a concentration of about 2 μg/ml in a PBS solution containing 5% by volume of fetal bovine serum. The resultant solution was dispensed in a unit volume of 50 μl to the wells and left standing at a temperature of 37° C. for one hour. The wells were washed with PBS. Then, a tris buffered solution (pH 7.4) containing 2,2'-azino-bis(3-ethylbenzothiazoline-6-sulfonic acid) in a concentration of 1 mmol/liter and also containing hydrogen peroxide in a concentration of 0.0045% by weight was dispensed in a unit volume of 100 μl into the wells and shaken at room temperature for 15 minutes to effect coloration. By testing the portions of solution in the individual wells for absorbance at wavelengths of 409 nm and 501 nm, it was found that a large difference of absorbance at the two wavelengths was present in the portions of solution in 49 of a total of 118 wells. From this result, it was concluded that the hybridomas which gave rise to the supernatants dispensed into these 49 wells produced human antibodies.

(4) Screening of Hybridoma Producing Human IgG Type Antibody Specific to AChR

The culture supernatants of the 49 hybridomas producing human antibodies in the step (3) above were tested for specificity to AChR by the RIA method. A tris buffered solution (pH 7.4), 50 ml in volume, containing the AChR extracted from 25 g of fetal bovine muscle and also containing 2% by volume of α-[4-(1,1,3,3-tetramethylbutyl) phenyl]-ω-hydroxy-poly(oxy-1,2-ethanediyl)] (produced by Sigma Corp, the U.S.A. and marketed under the tradename "Triton X-100") and α-Bungarotoxin labeled with $^{125}I$ possessing a specific activity of about 200 curies/mmol (produced by Amersham & Company, England) were mixed in amounts such as to register a radioactivity concentration of 200 nanocurie/ml. The resultant mixture was shaken at room temperature for about two hours. The mixture consequently obtained was added in a unit volume of 50 μl to 50 μl each of the culture supernatants of the aforementioned hybridomas and left standing overnight at a temperature of 4° C. Portions of the mixture consequently obtained, each combined with 50 μl of a solution prepared by diluting a rabbit anti-human IgG (γ-chain-specific) antiserum (produced by Hoechst, West Germany) with a tris buffered solution (pH 7.4) containing 0.1% by volume of Triton X-100 to twice the original volume, were left standing overnight at a temperature of 4° C. The formed precipitates were each washed three times with a tris buffered solution (pH 7.4) containing 0.1% by volume of Triton X-100 by centrifugation (at the rate of 3,000 rpm for a period of 20 minutes) and were tested for radioactivity with a gamma counter (produced by Aloka K. K. and marked under the tradename "Autowell Gamma System ARC-361"). The radioactivity data obtained for the precipitates (Sample Nos. 1 to 44) produced by using the culture supernatants of the 44 of a total of 49 hybridomas mentioned above are shown in FIG. 1. For comparison, a precipitate (Sample No. 45) which was produced following the procedure described above, except that the culture supernatant of $G(Ag_1)_2$-cl 7B strain was used in the place of the culture supernatant of a hybridoma, was tested for radioactivity. The results are also shown in FIG. 1. As noted from FIG. 1, the precipitate of Sample No. 10 was found to possess high radioactivity. It was therefore concluded that the supernatant which yielded this precipitate possessed a high reactivity to AChR and that the hybridoma which gave rise to this particular supernatant produced a human IgG type antibody specific to AChR.

(5) Cloning of Hybridoma

The hybridoma producing the human IgG type antibody specific to AChR, obtained in the step (4) above, was subjected to cloning by the limiting dilution method. This hybridoma was diluted with a RPMI-1640 medium containing about 13% by volume of fetal bovine serum in amounts such as to register concentrations of 50 cells/ml, 10 cells/ml, and 5 cells/ml. The diluted solutions of the concentrations of 50 cells/ml, 10 cells/ml, and 5 cells/ml were each dispensed in a unit volume of 0.1 ml respectively to 40 wells, 32 wells, and 24 wells in a covered 96-well microwell plate made of polystyrene (produced by Nunc Corp., Denmark) and subjected to stationary culture in air containing 7% of carbon dioxide at a temperature of 37° C. After two to four weeks' culture, cell colonies appeared in 17 wells of the plate. The supernatants of each wells which had produced such cell colonies were similarly tested for reactivity to AChR by the RIA method, to screen out one cell line which possessed a high ability to produce a human IgG type monoclonal antibody against AChR. This cell line was named as T/G-59(5C) strain.

(6) Purification of Human Monoclonal Antibody Produced from T/G-59(5C) strain

Figure 2:
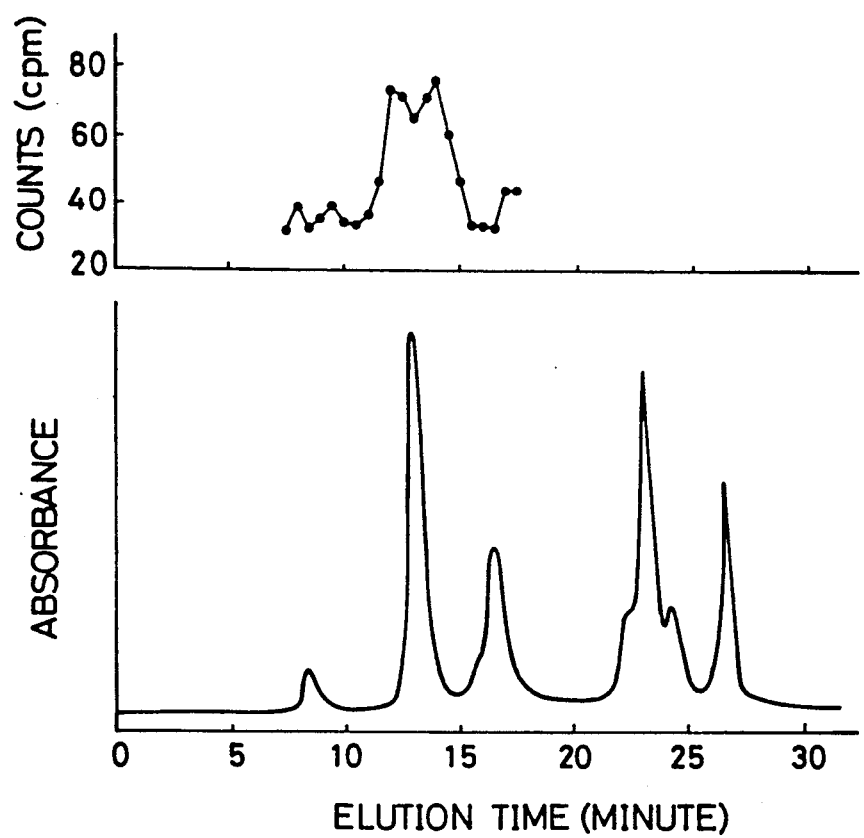
FIG. 2 shows the absorbancy, at a wavelength of 280 nm, of an eluate obtained by subjecting the culture supernatant of the T/G-59(5C) strain to gel permeation chromatography and the value of reactivity to AChR determined by the method of radioimmunoassay using a fraction of the eluate, both in Example (6).

The T/G-59(5C) strain obtained in the step of (5) above was suspended in a concentration of $1 \times 10^5$ cells/ml in a RPMI-1640 medium containing about 13% by volume of fetal bovine serum and cultured in air containing 7% of carbon dioxide at a temperature of 37° C. At the time that the cell concentration in the culture medium rose over $1 \times 10^6$ cells/ml, the cultured medium was centrifuged for separation of cells. The cells thus obtained were suspended in a concentration of $1 \times 10^5$ cells/ml in a tissue culture-quality serum-free culture medium (produced by Nippon Yakuhin Kaihatsu K. K. and marketed under the tradeneme "Hybrity-1") and cultured in air containing 7% of carbon dioxide at a temperature of 37° C. At the time that the cell concentration in the culture medium rose over $1 \times 10^6$ cells/ml, the cultured medium was centrifuged to obtain about 1.5 liters of a supernatant. This supernatant was concentrated with an ultrafiltration membrane possessing a fractional molecular weight of 10,000 (produced by Millipore Corp., the U.S.A. and marketed under the tradename "PTGC 043 10"), to obtain about 30 ml of a concentrate. The concentrate was subjected to gel permeation chromatography with a column packed with TSK gel G 3000SW (produced by Toyo Soda Manufacturing Co., Ltd.), using a 0.1 mol/liter sodium acetate buffered solution (pH 5.0) fed as an eluent at a flow rate of 1 ml/min, with the eluate fractionated at intervals of 30 seconds. The fractions were tested for reactivity to AChR by the RIA method in the same manner as in the step of (4). The eluates were tested for absorbance at the wavelength of 280 nm (absorption band specific to protein) and part of the aforementioned fractions were tested for reactivity to AChR. The results are shown in FIG. 2. The fractions occurring within 11.5 to 15.0 minutes' elution time and possessing reactivity to AChR and exhibiting a high absorbance at the wavelength of 280 nm were combined and subjected to affinity chromatography using a carrier (produced by LKB Produkter, Sweden and marketed under the tradename "Blue Trisacryl M") for removal of albumin. Part of the human IgG type monoclonal antibody consequently obtained was subjected to electrophoresis using polyacrylamide gel (composed of acrylamide and N,N'-methylene bisacrylamide at a gravimetric ratio of 37:1, having a gel concentration of 8% by weight) in the presence of sodium dodecyl sulfate (used in a concentration of 0.1% by weight). As a result, the human IgG type monoclonal antibody was found to possess a molecular weight of 180,000±20,000. The electrophoretic pattern of this human IgG type monoclonal antibody and that of a commercially available human IgG (produced by Miles Laboratories, the U.S.A. and marketed as Human IgG) are shown in FIG. 3 (1) and FIG. 3 (2) respectively. Based on the comparison of the absorbance, at a wavelength of 280 nm, of the PBS solution containing the human IgG type monoclonal antibody obtained by the aforementioned affinity chromatography and the absorbance at the same wavelength of the PBS solution containing 0.1% by weight of a commercially available human IgG, the amount of the human IgG type monoclonal antibody produced above was found to be about 4.9 mg.

(7) Determination of Subclass of Human IgG Type Monoclonal Antibody

Figure 4:
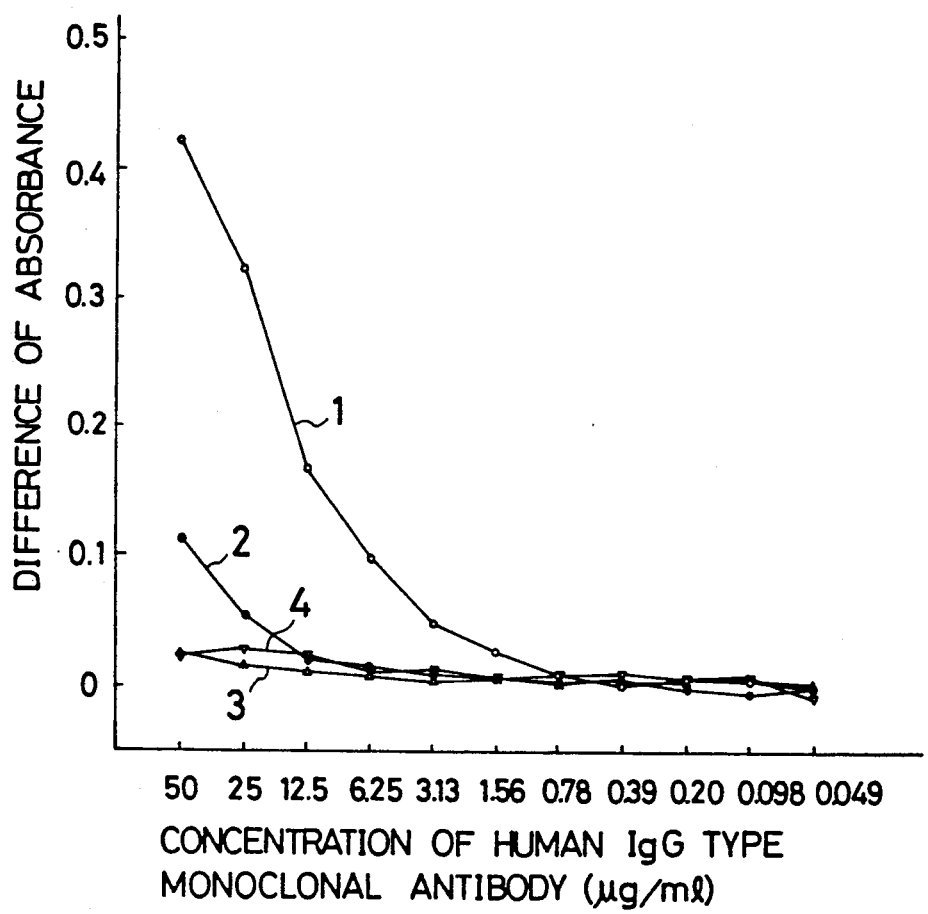
FIG. 4 shows the difference of absorbance at the two wavelengths, 409 nm and 501 nm, measured of each of the solutions obtained in the individual wells of a microwell plate by the procedure of coloration in Example (7).

The subclass of the human IgG type monoclonal antibody obtained in the step (6) above was determined by the ELISA method. The human IgG type monoclonal antibody was diluted with PBS to prepare a solution containing the antibody in a concentration of 50 μg/ml. Then by diluting this solution with PBS successively, each twice the former volume, there were obtained 11 solutions of concentrations successively decreased to 0.049 μg/ml. The solution of each of the concentrations was dispensed in a unit volume of 50 μl into four wells of a 96-well microwell plate made of polyvinyl chloride (produced by Becton-Dickinson Corp., the U.S.A. and marketed under the tradename "Falcon 3912") and left, standing overnight at a temperature of 4° C., to effect adsorption of a human IgG type monoclonal antibody on the plate. The solutions were removed from the wells. Then, a PBS solution containing 5% by volume of fetal bovine serum was dispensed in a unit volume of 300 μl into the wells and left standing at a temperature of 37° C. for two hours, to effect blocking of the solid-phase surface which had not adsorbed the human IgG type monoclonal antibody and then washed with a PBS solution containing 5% by volume of fetal bovine serum. Mouse monoclonal antibodies against human IgG$_1$ human IgG$_2$, human IgG$_3$, and human IgG$_4$ (produced by Bio-Yeda Corp., Israel and marketed under the tradenames "Monoclonal Anti-human IgG$_1$: Clone SG-11", "Monoclonal Anti-human IgG$_2$: Clone HP-6014", "Monoclonal Anti-human IgG$_3$: Clone HP-6050", and "Monoclonal Anti-human IgG$_4$: Clone HP-25") were each dissolved in a concentration of 5 μg/ml in a PBS solution containing 5% by volume of fetal bovine serum. The four mouse monoclonal antibody solutions consequently obtained were each dispensed in a unit volume of 50 μl into 11 wells having a human IgG type monoclonal antibody adsorbed in differing amounts and left standing at a temperature of 37° C. for one hour. Then, the wells were washed with a PBS solution containing 5% by volume of fetal bovine serum. An anti-mouse immunoglobulin antibody labeled with a horseradish-peroxidase (produced by Amersham & Company, England and marketed under the tradename "Anti-mouse Ig, Peroxidase-linked, Species-specific Whole Antibody") was dissolved in a concentration of about 2 μg/ml in a PBS solution containing 5% by volume of fetal bovine serum. The resultant solution was added in a unit volume of 50 μl to each of the wells and left standing at a temperature of 37° C. for one hour. The wells were cleaned with PBS. A tris buffered solution (pH 7.4) containing 2,2'-azino-bis(3-ethylbenzothiazoline-6-sulfonic acid) in a concentration of 1 mmol/liter and also containing 0.0045% by weight of hydrogen peroxide was dispensed in a unit volume of 100 μl to the wells and shaken at room temperature for 15 minutes, to induce coloration. Portions of the solution in the wells were tested for absorbance at wavelengths of 409 nm and 501 nm. The differences of absorbance at the two wavelengths consequently found are shown in a graph of FIG. 4.

In the graph, each curve represents the relation between the concentration of human IgG type monoclonal antibody and the difference of absorbance. Curves 1, 2, 3, and 4 represent the data for the wells into which the mouse monoclonal antibodies against the human IgG$_1$, human IgG$_2$, human IgG$_3$, and human IgG$_4$ had been dispensed. It is clearly noted from FIG. 4 that the human IgG type monoclonal antibody against AChR produced by the T/G-59(5C) strain was linked specifically with the mouse anti-human IgG$_1$ monoclonal antibody. Thus, the aforementioned human IgG type monoclonal antibody was concluded to belong to the IgG$_1$ subclass.

As clearly demonstrated by the foregoing working example, this invention permits efficient production of a novel human IgG$_1$ type monoclonal antibody specific to AChR by the use of a novel hybridoma.

What is claimed is:

1. Hybridoma strain T/G-59(5C) which is deposited with the Fermentation Research Institute under the accession number FERM BP-1798, obtained by the fusion of human cells which produce an antibody against nicotinic acetylcholine receptor with propagable human lymphoblastoid cell line G(Ag$_1$)$_2$-cl 7B, whereby said hybridoma produces a human IgG$_1$ monoclonal antibody which possesses a molecular weight on the range of 180,000±20,000 Daltons as measured under non-reducing conditions by the method of polyacrylamide gel electrophoresis performed in the presence of sodium dodecyl sulfate and is specific for nicotinic acetylcholine receptor.

2. A human IgG$_1$ monoclonal antibody which possesses a molecular weight in the range of 180,000±20,000 daltons as measured under non-reducing conditions by the method of polyacrylamide gel electrophoresis performed in the presence of sodium dodecyl sulfate and is specific for nicotinic acetylcholine receptor and wherein said antibody has been produced by hybridoma strain T/G-59(5C) which is deposited with the Fermentation Research Institute under the accession number FERM BP-1798.

* * * * *